US012622581B2

(12) United States Patent
Tatur et al.

(10) Patent No.: US 12,622,581 B2
(45) Date of Patent: May 12, 2026

(54) DEVICE AND METHOD FOR EVALUATING A PERFORMANCE OF A VISUAL EQUIPMENT

(71) Applicant: Essilor International, Charenton-le-pont (FR)

(72) Inventors: Guillaume Tatur, Charenton-le-pont (FR); Laurent Calixte, Charenton-le-pont (FR); Sébastien Fricker, Charenton-le-pont (FR); Bénédicte Deldalle, Charenton-le-pont (FR); Gildas Marin, Charenton-le-pont (FR)

(73) Assignee: Essilor International, Charenton-le-pont (FR)

( * ) Notice: Subject to any disclaimer, the term of this patent is extended or adjusted under 35 U.S.C. 154(b) by 306 days.

(21) Appl. No.: 18/546,149

(22) PCT Filed: Jan. 13, 2022

(86) PCT No.: PCT/EP2022/050613
§ 371 (c)(1),
(2) Date: Aug. 11, 2023

(87) PCT Pub. No.: WO2022/171376
PCT Pub. Date: Aug. 18, 2022

(65) Prior Publication Data
US 2024/0115125 A1    Apr. 11, 2024

(30) Foreign Application Priority Data
Feb. 12, 2021    (EP) ..................................... 21305189

(51) Int. Cl.
*A61B 3/00* (2006.01)
*G06Q 10/0639* (2023.01)

(52) U.S. Cl.
CPC ..... *A61B 3/0025* (2013.01); *G06Q 10/06395* (2013.01)

(58) Field of Classification Search
CPC ............................ A61B 3/0025; A61B 3/113; G06Q 10/06395; G06Q 10/06
(Continued)

(56) References Cited

U.S. PATENT DOCUMENTS 7,980,692 B2 *    7/2011    Fisher .................... G02C 7/061
                                                351/159.74
2013/0293844 A1 *    11/2013    Gross .................... A61B 5/1114
                                                351/209
(Continued)

FOREIGN PATENT DOCUMENTS

JP        2005-513526 A    5/2005
WO    WO-2013059331 A1 *    4/2013    ............. G16H 80/00
(Continued)

OTHER PUBLICATIONS

International Search Report & Written Opinion issued Feb. 23, 2022 in PCT/EP2022/050613, filed on Jan. 13, 2022, citing documents 1-4 & 15-16 therein, 14 pages.
(Continued)

*Primary Examiner* — Mohammed A Hasan
(74) *Attorney, Agent, or Firm* — Oblon, McClelland, Maier & Neustadt, L.L.P.

(57) ABSTRACT

A device for evaluating the performance of visual equipment for a wearer. The device includes at least one input adapted to obtain virtual tests to be performed with the equipment, each test including at least one scenario combined with at least one virtual model of the wearer, defining how a visual task including a sequence of fixation points is to be carried out by the model in an environment defined by a description of shapes and positions of elements to be viewed by the
(Continued)

model, at least one processor configured for selecting at least one test, based on at least one personalized real or simulated wearer activity profile representing usage of the equipment by the wearer, and evaluating the performance of the equipment with which the selected test is performed by the model by computing for one or more fixation points at least one performance criterion generated for the task.

15 Claims, 2 Drawing Sheets

(58) Field of Classification Search
USPC .......................................................... 351/206
See application file for complete search history.

(56) References Cited

U.S. PATENT DOCUMENTS

| | | | |
|---|---|---|---|
| 2014/0285769 A1 | 9/2014 | Palanker et al. | |
| 2015/0169953 A1* | 6/2015 | Border ................... | G06V 40/19 |
| | | | 348/78 |
| 2016/0213243 A1 | 7/2016 | Palanker et al. | |
| 2017/0143202 A1 | 5/2017 | Palanker et al. | |
| 2018/0121608 A1* | 5/2018 | Gross ..................... | G16H 20/30 |
| 2018/0256023 A1* | 9/2018 | Swital ................ | G06Q 30/0621 |
| 2020/0146546 A1* | 5/2020 | Chene ................... | A61B 3/0008 |
| 2020/0151869 A1* | 5/2020 | Hu ......................... | G06F 9/4881 |
| 2021/0153736 A1 | 5/2021 | Palanker et al. | |

FOREIGN PATENT DOCUMENTS

| | | | | |
|---|---|---|---|---|
| WO | WO 2018/074528 A1 | 4/2018 | | |
| WO | WO 2020/193370 A1 | 10/2020 | | |
| WO | WO-2020193436 A1 * | 10/2020 | ........ | G01M 11/0264 |
| WO | WO-2024227576 A1 * | 11/2024 | ............. | A61B 3/113 |

OTHER PUBLICATIONS

Japanese Office Action issued Aug. 26, 2025, in corresponding Japanese Patent Application No. 2023-543013 (with English Translation), citing documents 15-17 therein, 9 pages.
European Communication pursuant to Article 94(3) EPC issued Dec. 9, 2025, in corresponding European Patent Application No. 21 305 189.9, citing documents 2 and 3 therein, 9 pages.
Anonymous: "Glasses—Wikipedia", Feb. 11, 2021, XP093312082, Retrieved from the Internet: URL:https://en.wikipedia.org/w/index. php?title=Glasses&oldid=1006210819 [retrieved on Sep. 8, 2025], pp. 1-19.
Anonymous: "Bildschirmarbeitsplatzbrille—Wikipedia", Jun. 2020, XP093312106, Retrieved from the Internet: URL:https://de.wikipedia. org/w/index.php?title=Bildschirmarbeitsplatzbrille&oldid= 200969736 [retrieved on Sep. 8, 2025], pp. 1-4.

* cited by examiner

DEVICE AND METHOD FOR EVALUATING A PERFORMANCE OF A VISUAL EQUIPMENT

FIELD OF THE DISCLOSURE

The present disclosure relates to a device and method for evaluating a performance of a visual equipment intended for a wearer of that visual equipment.

BACKGROUND OF THE DISCLOSURE

Nowadays, the performance of a piece of visual equipment such as an ophthalmic lens or a solar lens may be evaluated by using a number of criteria, among which sharpness of vision, distortions, or other criteria for example related to binocular vision.

In this respect, eyeglasses simulation methods are known, in which the customer can try and subjectively evaluate equipment in a virtual environment through a virtual reality device. Such an eyeglasses wearing simulation method and device is disclosed by document EP-A-2 749 207.

However, no objective evaluation of the performance of visual equipment is carried out.

Besides, the evaluation of the performance of a piece of visual equipment through simulations is a non-trivial issue. Optical characteristics are not fully representative of the performance of a piece of visual equipment as perceived by the wearer. Indeed, a wearer will use the piece of visual equipment in various situations and environments, experiencing functional characteristics of the equipment such as field width and sharpness in the different vision zones, geometrical and optical flow distortion, comfort area as well as internal state considerations such as efforts related to posture and to binocular vision.

Human wearer tests are another known solution for evaluating the performance of a piece of visual equipment. In particular, in certain types of wearer tests, known as "in-lab tests", human wearers are asked to carry out specific tasks while wearing the piece of visual equipment to be evaluated, such as reading, walking, performing a precision task, etc.

This implies lengthy testing processes that do not necessarily take into account the specificity of the wearer's visual habits or the specific way in which each wearer uses visual equipment.

More generally, the above known solutions do not make it possible to obtain an overall estimate of the performance of visual equipment.

Document WO 2020/193436 A1 discloses a device and method for evaluating a performance of a piece of visual equipment intended for a human wearer to carry out a visual task. The described device and method involve a virtual "avatar" that is a virtual model of the human wearer, in addition to virtual models of the visual task and of the scene where the virtual, simulated visual task is to be carried out. This makes it possible to apply the performance evaluation to a given wearer population i.e. groups of wearers considered to have similar characteristics. Thus, that solution avoids the burden of repeating tests on various individuals.

However, although such evaluation is made in a potentially efficient and economic manner for groups of wearers thanks to the "avatar", it does not take account of the very specific habits of each individual wearer.

Namely, a given individual, although having comparable characteristics to other individuals of a defined group of wearers, may nevertheless wear and use the piece of visual equipment differently from other individuals in the same group of wearers. For example, a given individual may wish to use the piece of visual equipment for other visual tasks than the one for which the performance has been evaluated and those other visual tasks will not necessarily be the same as for the other individuals of the same group of wearers. In addition, the other visual tasks will possibly be carried out in environments differing from the one for which the performance has been evaluated, with different distances to objects of the scene, different lighting, far vision instead of near vision, etc.

Furthermore, instead of having a single choice i.e. the piece of visual equipment for which the evaluated performance is considered to be the "best", each individual may wish to select his/her preferred piece of visual equipment depending on his/her own personal criteria, among a preselection of various propositions and recommendations made by an ECP (Eye Care Professional), either in a shop, or online.

Thus, there is a need for further customizing the piece of visual equipment to each given individual, in order to provide for each individual, rather than a "ready-to-wear" piece of visual equipment, the possibility of wearing "made-to-measure" visual equipment, taking account of both the individual per se and the individual's visual task habits and intended uses of such visual equipment, thanks to an overall personalized evaluation of the visual equipment performance for that individual.

SUMMARY OF THE DISCLOSURE

An object of the disclosure is to overcome the above-mentioned drawbacks of the prior art.

To that end, the disclosure provides a device for evaluating a performance of a visual equipment intended for a wearer, wherein the device comprises:

at least one input adapted to obtain a plurality of virtual tests to be performed with the visual equipment, each virtual test of the plurality of virtual tests comprising at least one scenario combined with at least one virtual model of the wearer, the scenario defining how a predetermined visual task comprising a sequence of fixation points is to be carried out by the at least one virtual model in an environment defined by a description of shapes and positions of elements to be viewed by the at least one virtual model of the wearer;

at least one processor configured for:

selecting at least one virtual test among the plurality of virtual tests, based on at least one personalized real or simulated wearer activity profile representing usage of the visual equipment by the wearer;

evaluating the performance of the visual equipment with which the selected at least one virtual test is performed by the at least one virtual model of the wearer, by computing for at least one of the fixation points at least one predetermined performance criterion generated for the predetermined visual task.

Therefore, firstly, the device according to the disclosure makes it possible to select in an automated manner, having regard to the activity profile of a given individual, the most appropriate virtual test(s) among a series of virtual tests that involve simulation context and evaluation criteria considered relevant for evaluating a visual equipment performance for that given individual, who is the wearer of such visual equipment.

Secondly, the device makes it possible to evaluate, also in an automated manner, the mentioned visual equipment performance, based on at least one performance criterion that is related to the visual task considered.

Thus, the definitions of the visual task to be simulated through virtual tests, of the simulated environment and of the performance criteria are all customized for each given individual.

In an embodiment of the above-defined device where the wearer is a given individual, the at least one virtual model of the wearer comprises a virtual model of that given individual.

In that embodiment, the plurality of virtual tests may comprise multiple scenarios combined with the virtual model of the given individual.

In another embodiment of the device where the wearer pertains to a group of wearers defined by general characteristics, individual characteristics of each wearer of the group being unknown, the at least one virtual model of the wearer comprises a plurality of virtual models of wearers that is representative of that group of wearers.

In that embodiment, the plurality of virtual tests may comprise either a single scenario combined with the plurality of virtual models of wearers, or multiples scenarios combined with the plurality of virtual models of wearers.

In an embodiment, the personalized wearer activity profile comprises different weights assigned to the at least one scenario and/or to the at least one predetermined performance criterion depending on the relevance of the at least one scenario and/or of the at least one criterion for the wearer in the above-mentioned usage of the visual equipment.

In an embodiment, the virtual model of the wearer comprises a virtual model of at least one eye of the wearer, a virtual model of the head of the wearer and a virtual model of the torso of the wearer.

In an embodiment, the predetermined performance criterion comprises at least one of visual acuity criteria, distortion criteria and visual behavior criteria evaluating the head and eyes coordination.

In that embodiment, the at least one predetermined performance criterion may involve either monocular or binocular vision.

In an embodiment, the at least one scenario comprises at least a first scenario for which the predetermined visual task is a far vision task and the at least one predetermined performance criterion is visual acuity, a second scenario for which the predetermined visual task is an intermediate vision task and the at least one predetermined performance criterion is visual acuity, a third scenario for which the predetermined visual task is a near vision task and the at least one predetermined performance criterion is visual acuity, and a fourth scenario for which the at least one predetermined performance criterion is a distortion criterion.

The disclosure also provides a method for evaluating a performance of a visual equipment intended for a wearer, wherein the method comprises:

obtaining at least one virtual model of the wearer;
obtaining a plurality of virtual tests to be performed with the visual equipment, each virtual test of the plurality of virtual tests comprising at least one scenario combined with the at least one virtual model of the wearer, the scenario defining how a predetermined visual task comprising a sequence of fixation points is to be carried out by the at least one virtual model in an environment defined by a description of shapes and positions of elements to be viewed by the at least one virtual model of the wearer;

selecting by at least one processor at least one virtual test among the plurality of virtual tests, based on at least one personalized real or simulated wearer activity profile representing usage of the visual equipment by the wearer;
evaluating by the at least one processor the performance of the visual equipment with which the selected at least one virtual test is performed by the at least one virtual model of the wearer, by computing for at least one of the fixation points at least one predetermined performance criterion generated for the predetermined visual task.

In particular embodiments, that method for evaluating is executed by the device for evaluating according to the disclosure, in any of its embodiments.

In an embodiment of the method where the wearer is a given individual, the at least one virtual model of the wearer comprises a virtual model of that given individual.

In that embodiment, the plurality of virtual tests may comprise multiple scenarios combined with the virtual model of the given individual.

In another embodiment of the method where the wearer pertains to a group of wearers defined by general characteristics, individual characteristics of each wearer of the group being unknown, the at least one virtual model of the wearer comprises a plurality of virtual models of wearers that is representative of that group of wearers.

In that embodiment, the plurality of virtual tests may comprise either a single scenario combined with the plurality of virtual models of wearers, or multiples scenarios combined with the plurality of virtual models of wearers.

In an embodiment of the method, the personalized wearer activity profile comprises different weights assigned to the at least one scenario and/or to the at least one predetermined performance criterion depending on the relevance of the at least one scenario and/or of the at least one criterion for the wearer in the above-mentioned usage of the visual equipment.

In an embodiment of the method, the virtual model of the wearer comprises a virtual model of at least one eye of the wearer, a virtual model of the head of the wearer and a virtual model of the torso of the wearer.

The disclosure further provides a computer program product for evaluating a performance of a visual equipment intended for a wearer, wherein it comprises one or more sequences of instructions that are accessible to a processor and that, when executed by the processor, cause the processor to:

obtain at least one virtual model of the wearer;
obtain a plurality of virtual tests to be performed with the visual equipment, each virtual test of the plurality of virtual tests comprising at least one scenario combined with the at least one virtual model of the wearer, the scenario defining how a predetermined visual task comprising a sequence of fixation points is to be carried out by the at least one virtual model in an environment defined by a description of shapes and positions of elements to be viewed by the at least one virtual model of the wearer;
select at least one virtual test among the plurality of virtual tests, based on at least one personalized real or simulated wearer activity profile representing usage of the visual equipment by the wearer;
evaluate the performance of the visual equipment with which the selected at least one virtual test is performed by the at least one virtual model of the wearer, by computing for at least one of the fixation points at least one predetermined performance criterion generated for the predetermined visual task.

The disclosure further provides a non-transitory computer-readable storage medium, wherein it stores one or more sequences of instructions that are accessible to a processor and that, when executed by the processor, cause the processor to:

obtain at least one virtual model of the wearer;

obtain a plurality of virtual tests to be performed with the visual equipment, each virtual test of the plurality of virtual tests comprising at least one scenario combined with the at least one virtual model of the wearer, the scenario defining how a predetermined visual task comprising a sequence of fixation points is to be carried out by the at least one virtual model in an environment defined by a description of shapes and positions of elements to be viewed by the at least one virtual model of the wearer;

select at least one virtual test among the plurality of virtual tests, based on at least one personalized real or simulated wearer activity profile representing usage of the visual equipment by the wearer;

evaluate the performance of the visual equipment with which the selected at least one virtual test is performed by the at least one virtual model of the wearer, by computing for at least one of the fixation points at least one predetermined performance criterion generated for the predetermined visual task.

As the advantages of the method, of the computer program product and of the computer-readable storage medium are similar to those of the device, they are not repeated here.

The computer program product and the computer-readable storage medium are advantageously configured for executing the method in any of its execution modes.

BRIEF DESCRIPTION OF THE DRAWINGS

For a more complete understanding of the description provided herein and the advantages thereof, reference is now made to the brief descriptions below, taken in connection with the accompanying drawings and detailed description, wherein like reference numerals represent like parts.

DETAILED DESCRIPTION OF EMBODIMENTS

Figure 1:
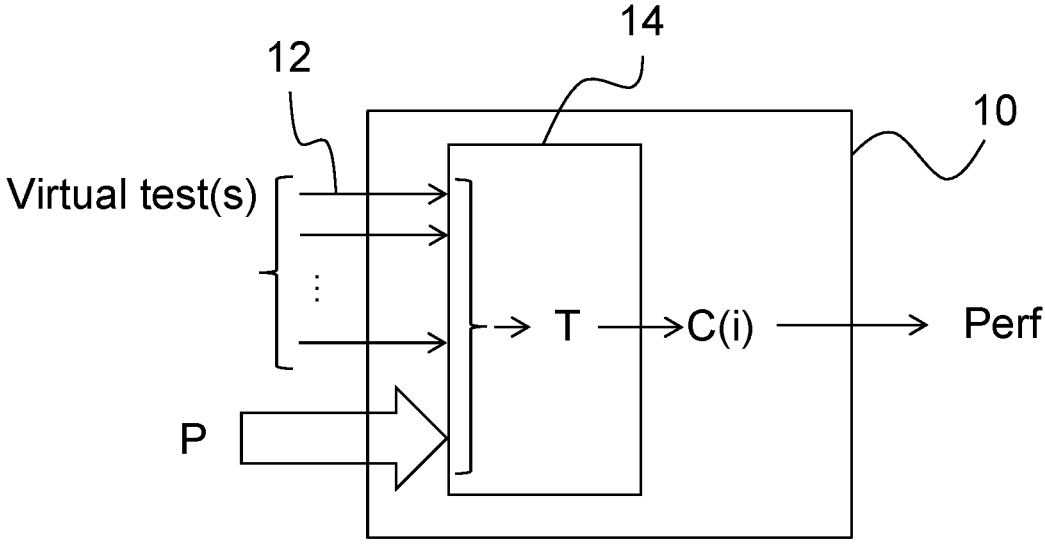
FIG. 1 is a schematic view of a device according to the disclosure, in a particular embodiment.

In the description which follows, the drawing figures are not necessarily to scale and certain features may be shown in generalized or schematic form in the interest of clarity and conciseness or for informational purposes. In addition, although making and using various embodiments are discussed in detail below, it should be appreciated that as described herein are provided many inventive concepts that may embodied in a wide variety of contexts. Embodiments discussed herein are merely representative and do not limit the scope of the disclosure. It will also be obvious to one skilled in the art that all the technical features that are defined relative to a process can be transposed, individually or in combination, to a device and conversely, all the technical features relative to a device can be transposed, individually or in combination, to a process.

The terms "comprise" (and any grammatical variation thereof, such as "comprises" and "comprising"), "have" (and any grammatical variation thereof, such as "has" and "having"), "contain" (and any grammatical variation thereof, such as "contains" and "containing"), and "include" (and any grammatical variation thereof such as "includes" and "including") are open-ended linking verbs. They are used to specify the presence of stated features, integers, steps or components or groups thereof, but do not preclude the presence or addition of one or more other features, integers, steps or components or groups thereof. As a result, a method, or a step in a method, that "comprises", "has", "contains", or "includes" one or more steps or elements possesses those one or more steps or elements, but is not limited to possessing only those one or more steps or elements.

As shown in FIG. 1, in a particular embodiment, a device 10 for evaluating a performance of "a visual equipment" i.e. a piece or item of visual equipment intended for a wearer, i.e. a human being wearing that visual equipment or a theoretical wearer having defined characteristics but not corresponding to any specific known existing person, comprises one or more inputs 12.

The visual equipment may be an ophthalmic lens or pair of ophthalmic lenses, or a solar lens or pair of solar lenses, or an ophthalmic solar lens or pair of ophthalmic solar lenses. It may be in the form of eyeglasses or contact lenses.

The one or more inputs 12 are adapted to obtain a plurality of virtual tests to be performed, as described in more detail below, with that visual equipment.

Each virtual test of the plurality of virtual tests comprises at least one so-called "scenario" that is combined with at least one virtual model of the wearer.

In the present disclosure, the virtual model of the wearer is also referred to as an "avatar" of the wearer. It may be built as described in document WO 2020/193436 A1, or it may consist of pre-recorded data obtained from a database, as proposed in document WO 2020/193370 A1.

In the present disclosure, a scenario defines how a predetermined visual task comprising a sequence of fixation points is to be carried out by the at least one avatar in an environment defined by a description of shapes and positions of elements to be viewed by the avatar.

Each virtual test represents the execution of a scenario by an avatar and resulting values of at least one performance evaluation criterion.

A virtual evaluation of the performance of the visual equipment corresponds to a collection of virtual tests comprising at least one virtual test. The virtual tests may consist of multiple scenarios for a same avatar, or to one scenario applied to multiple avatars, or to multiple scenarios applied to multiple avatars.

As a non-limiting example, the environment may comprise a room, furniture, landscape, objects and may carry additional attributes such as the visual characteristics of its components, e.g. luminance, contrast, color, etc.

The scenario may include the environment and the visual task.

The sequence of fixation points comprised in the visual task, which is also referred to as "task", may be associated with components of the environment.

An avatar executes the task by fixating each point in a defined order. Thus, the avatar is used to simulate the execution of a scenario by a wearer.

In an embodiment, the avatar may comprise a virtual model of at least one eye of the wearer, a virtual model of the head of the wearer and a virtual model of the torso of the wearer.

In an embodiment, the wearer is a given individual, in which case the at least one avatar comprises a virtual model of that given individual. In such a case, the avatar corresponds to a real person, sharing characteristics with that person.

In that embodiment, the plurality of virtual tests may comprise multiple scenarios combined with the virtual model of the given individual.

Alternatively, the wearer may pertain to a group of wearers defined by general characteristics, individual characteristics of each wearer of that group being unknown. In that case, the at least one avatar comprises a plurality of virtual models of wearers that is representative of that group of wearers. In such a case, the avatar corresponds to a group of persons.

In that embodiment, the plurality of virtual tests may comprise, either a single scenario combined with the plurality of virtual models of wearers, or multiple scenarios combined with the plurality of virtual models.

In still another embodiment, the wearer may not be an existing person, but a predefined average wearer, in which case the characteristics of the avatar correspond to those of that average wearer.

The sequence of fixation points may have additional attributes such as the time instant at which each point is to be seen by the avatar, the minimum visual acuity with which each point is to be seen, etc.

The scenario also defines the above-mentioned at least one performance criterion to be considered for evaluating the performance of the visual equipment for at least one of the fixation points. In other words, at least one predetermined performance criterion is generated for the predetermined visual task through execution of each scenario by one or several avatars.

The scenario also defines the position of the avatar in the environment. The position may be static during the execution of the scenario. Alternatively, the avatar may be moving during the execution of the scenario. As a non-limiting example, the avatar may be walking, running, climbing stairs, driving a car, etc.

The scenario may also define a motion of one or more components of the environment as a function of time. By way of non-limiting example, a ball is moving during a game. If a fixation point is attached to the ball, its position will also vary with time.

Thus, the device 10 makes it possible to obtain one or a collection of scenarios that each combine a visual task, an environment and one or more performance criteria to be evaluated. Such collection of tasks, environments and performance criteria may be based on items of a wearer test evaluation form, consisting of a number Q of questions rated on a given N-point scale, Q and N being non-null integers.

The evaluation form may emphasize specific characteristics of the visual equipment, or general everyday life usages of the equipment.

The device according to the present disclosure further comprises at least one processor 14, which is configured for selecting at least one virtual test T among the plurality of virtual tests, based on at least one personalized real or simulated wearer activity profile P representing usage of the visual equipment by the wearer, as described in more detail below.

In an embodiment, the personalized activity profile P of the wearer makes it possible to customize the selection of scenarios.

In an embodiment, the personalized wearer activity profile P may comprise different weights assigned to the at least one scenario and/or to the at least one predetermined performance criterion depending on the relevance of the at least one scenario and/or of the at least one criterion for the wearer in the usage of the visual equipment.

In other words:
- a score weight may be assigned to each scenario for reflecting how much the scenario is representative of the wearer's everyday usage of the equipment;
- the personalized wearer activity profile P may also serve to weight the performance criteria associated with each scenario according to their importance for the wearer considered.

The personalized wearer activity profile P may be generated in different manners:
- from a declarative survey or questionnaire, or
- using various techniques, such as techniques relying on a "smartframe" (i.e. a spectacle frame with additive functionalities provided by a sensor or a set of sensors that record information about visual equipment usage such as activities, environment, light conditions, etc.), or on a "clip-on" device (i.e. a sensor or set of sensors that can be attached to a spectacle frame and that also record information about visual equipment usage), or
- from large or Big Data databases.

The above-mentioned virtual environment may be personalized to match the human or theoretical wearer's usual real environment and may be automatically customized using anatomical parameters of the wearer, such as the Harmon distance. This may be done using the declarative survey or questionnaire, computer-assisted environment parameterization, or by positioning a real-world environment, for example through tridimensional scan or motion capture.

The processor 14 is further configured for evaluating the performance, denoted Perf on the drawing, of the visual equipment with which the selected at least one virtual test T is performed by the at least one avatar, by computing for at least one of the fixation points, denoted i on the drawing, the at least one predetermined performance criterion $C(i)$ generated for the predetermined task.

In an embodiment, the predetermined performance criterion $C(i)$ may comprise at least one of visual acuity criteria, distortion criteria and visual behavior criteria evaluating the head and eyes coordination. By way of non-limiting example, the performance criterion $C(i)$ may involve monocular vision. As another non-limiting example, the performance criterion $C(i)$ may involve binocular vision.

Thus, the processor 14 of the device 10 provides a global performance evaluation by combining the performance criteria resulting from each virtual test.

For example, depending on the embodiment, the at least one scenario may be a set of scenarios comprising at least one of the following, the list being non-exhaustive:
- a first scenario where the task is a far vision task and the performance criterion is visual acuity,
- a second scenario where the task is an intermediate vision task and the performance criterion is visual acuity,
- a third scenario where the task is a near vision task and the performance criterion is visual acuity,
- a fourth scenario where the performance criterion is a distortion criterion.

The manner in which the scenarios may be defined is described in more detail below.

A list of functional characteristics of a piece of visual equipment used by a wearer is provided. These functional characteristics are the various performance items that it is desired to evaluate.

For each functional characteristic, a scenario considered to be relevant for evaluating that characteristic is defined.

For instance, to evaluate reading/writing performance and comfort, the following scenarios may be defined: reading on various reading supports, such as a book, paper, tablet screen, smartphone screen, journal, etc. while being subject to various postural conditions or environmental constraints such as being seated in a couch or table, standing, lying down, etc. and evaluate various comfort and performance criteria, such as visual acuity, width of vision field, distortion, postural flexibility, etc.

A list of functional characteristics to evaluate, in the non-limiting example of a progressive lens equipment for a presbyope wearer, is provided below.

List of Functional Characteristics to Evaluate for a Progressive Lens Equipment for a Presbyope Wearer:

Q1. Clarity of vision in far vision

Q2. Clarity of vision in Intermediate vision

Q3. Clarity of vision in near vision

Q4. Transitions between far vision and near vision

Q5. Distortions when the wearer moves

List of Generic Scenario Types:

The following generic scenarios are adapted to evaluate the functional characteristics of an equipment:

Reading scenarios: reading on various objects/supports while in various postural conditions or environmental constraints and evaluate various visual acuity and visual behavior criteria;

Fixation scenarios: looking at various objects/supports, or at several points on a widely extended object, while in various postural conditions or environmental constraints and evaluate various visual acuity and visual behavior criteria.

Transition scenarios: transiting from a first reading or fixation task to a second reading or fixation task at a different distance but in the same postural conditions or environmental constraints and evaluate various visual acuity and visual behavior criteria.

Eye or head motion based scenarios: holding gaze on various objects, static or moving, while moving only head and eyes and evaluating various visual acuity, visual behavior and distortions criteria.

Locomotion scenarios: body displacement by various locomotion means while performing fixation tasks and evaluating various visual acuity, visual behavior and distortions criteria.

Non-limiting list of examples of various objects/supports, each with specific field of view and/or vision related requirements (e.g. visual acuity, contrast, reader visual span): book, paper, tablet, smartphone, journal, television, person, in-car navigation device, laptop screen, desktop screen, advertising hoarding, traffic sign, sign post, visual acuity chart, cinema screen (widely extended object), landscape (widely extended object).

Rather than building an exhaustive list of objects, interesting features to define for optimizing personalization are the positions, the dimensions and the visual characteristics of the objects.

Non-Limiting List of Examples of Various Postural Conditions:

Base posture: seated in a couch, in a car or in front of a table; standing; lying down in a bed.

Postural limitations: free head and torso motion; free head motion, limited torso motion (e.g. when sitting in a car); limited head and trunk motion (e.g. when lying in bed).

Non-Limiting List of Examples of Environmental Constraints:

Object distance: within arm's reach, on physical support (e.g. table), distance at room scale, street scale or landscape.

Object alignment/orientation: behavior habit depending on laterality for instance, support-dependent alignment or orientation.

Object distribution in space: aligned with wearer sagittal plane; aligned with wearer fronto-parallel plane; unconstrained alignment; narrow or wide location spread; regular, model-based or random object locations.

Non-Limiting List of Examples of Various Performance Criteria:

Visual acuity criteria, which evaluate the sharpness of vision through and around central vision: visual acuity (or visual acuity loss), preferably but not necessarily binocular, field of view, visual acuity extent (i.e. the extent of the area that is seen clearly when using central vision by moving the eye, but not the head), contrast sensitivity.

Visual behavior criteria, which evaluate the head and eyes coordination through the relationship between eye accommodations, gaze directions and head position: head posture efforts and gaze posture efforts as described in WO 2020/193436 A1, convergence and accommodation efforts, head freedom area.

Distortion criteria, which evaluate the deformation of perception of space through peripheral vision: static distortions, dynamic distortions, optical/retinal flow, depth perception.

The manner in which the personalized wearer activity profile P may be defined is described in more detail below.

The profile P is defined so as to make it possible for the device 10, either to filter the list of scenarios in order to personalize the selection of scenarios, or to assign a score weight to each scenario so that the resulting weighted collection of scenarios is the best representation of the wearer's everyday usage of the equipment.

Furthermore, dominant performance criteria i.e. performance criteria that are meaningful to the wearer will be ranked or will also be associated with a weight, to account for wearer preferences.

The profile P includes usage of the equipment and lifestyle of the wearer. By way of non-limiting example, the profile P may include:

a list of tasks or activities performed by the considered wearer;

a weighting of the tasks, which may represent the amount of each task in the wearer's life, or the importance of each task to the wearer;

the weighting of the performance criteria according to the importance the wearer attributes to each performance criterion.

Non-Limiting Example of Profile P:

smartphone for watching videos and gaming, usually in couch, usage frequency: low;

laptop for office work, usage frequency: high;

reading book usually in public transportation, usage frequency: medium;

bicycle for sport, usage frequency: high;

size 1.75 m, Harmon's distance 0.41 m;

all performance criteria are equally important.

A list of scenarios is defined, where each scenario is intended to evaluate one of the functional characteristics of the equipment. In the below non-limiting examples of scenarios, personalization and standard values are provided between brackets along with the technique used for personalization: [standard value, personalized value, personalization technique]. The personalization techniques are described in more detail after the below list of scenarios.

Scenario 1—Clarity of Far Vision—Generic Scenario Type: Fixation

Looking at several objects at 10 m located in a field of view of 120° horizontally and 40° vertically for a wearer with size [1.68 m, 1.75 m, applying custom wearer size] when standing in a street environment. These objects require a minimum visual acuity of 9/10 to be seen correctly. Performance criteria are the evaluation of visual acuity in foveal vision and postural efforts while fixating every object. The fixation points are distributed according to various patterns.

Scenario 2—Clarity of Intermediate Vision—Generic Scenario Type: Fixation

Reading on a laptop screen at 0.70 m placed on a desk of standard height when seating on a chair of standard height in front of the desk. The standard height for desk and chair is 0.72 m+/−0.015 m according to standard NF EN 527-1 D62-044-1, August 2011. Eye level is determined using the height of the chair and the wearer's seating height [0.87 m, 0.91 m, seating height as a function of size based on body measurements surveys]. This object (laptop screen) contains a set of characters which require a minimum visual acuity of 9/10 to be seen correctly. Performance criteria are the evaluation of visual acuity in foveal vision and postural efforts on each fixation point as distributed on the object according to a natural reading pattern.

Scenario 3—Clarity of Near Vision—Generic Scenario Type: Fixation

Reading a book held in hands at [0.38 m, 0.41 m, using Harmon distance estimate, as a function of wearer's height and any conventional body link measurements model] when sitting [on a chair in a room, in public transportation inducing oscillations of the book compared to the head, scenario environment personalized to wearer's profile P]. This object (book) contains a set of characters which require a minimum visual acuity of 9/10 to be seen correctly. Performance criteria are the evaluation of visual acuity in foveal vision and postural efforts on each fixation point as distributed on the object according to a natural reading pattern.

Scenario 4—Transition Between Far Vision and Near Vision—Generic Scenario Type: Transitions Transiting from reading a book held in hands at [0.38 m, 0.41 m, using Harmon distance estimate as a function of wearer's height and any conventional body link measurements model] to looking at objects at various proximities (at least 4 m: far vision) while being seated. The evaluated performance criteria are postural efforts and head freedom area. The term "head freedom area" refers to a range of head positions the wearer of an optical lens can adopt without losing optical performance beyond a certain predefined value when looking at a specific point through the optical lens, as described in WO 2020260481 A1.

Scenario 5—Distortions—Generic Scenario Type: Locomotion

Wearer with size [1.68 m, 1.75 m, applying custom wearer size] walking in a street while looking at various objects at various distances and positions and evaluating static and dynamic distortion criteria.

The results of each scenario may be scaled with a weight value that may then be personalized to take into account the interest or activities of the considered wearer.

The personalization of scenarios and of weights is now described in more detail in particular embodiments.

Working distance when reading a book (denoted DistanceBook below), and thus object/environment proximities, may be personalized according to the wearer's Harmon distance (denoted HarmonDistance below):

$$DistanceBook=HarmonDistance.$$

Working distance when looking at a smartphone screen (denoted DistanceSmartphone below) may be personalized according to the wearer's Harmon distance, for example as follows:

$$DistanceSmartphone=80\%\times HarmonDistance$$

Avatar's heights when sitting or standing in various scenarios may be personalized according to the size provided in the wearer's profile P and any conventional model of body link lengths as a function of the person's size.

Supports, objects, postural conditions and environmental constraints in the different scenarios may be adapted according to activities and usages provided in the wearer's profile P, for example in scenario 3 (Reading on a book in public transportation).

Weights of the scenarios may be personalized according to activities and usages provided in the wearer's profile P, for example as follows: high weights for scenario 5, due to high frequency of outdoor activity including fast locomotion, such as cycling; high weight for scenario 2, due to high frequency of working on a laptop; medium weight for scenario 3, due to medium frequency of reading books.

Weights of the performance criteria may be personalized according to the wearer's preferences regarding equipment performance requirements. In the non-limiting example given in the present disclosure, all the performance criteria are equally important.

Following the computing, by the processor 14, for at least one of the fixation points, of at least one predetermined performance criterion generated for the predetermined visual task, global and detailed performances can be computed based on the weights previously defined.

Detailed performances refer to the objective evaluation of each functional characteristic, whereas global performance is a value that best represents the overall performance of the piece of visual equipment taking account of the wearer's preferences regarding equipment usage.

In the previously described non-limiting example, let us denote Sj, j=1, . . . , 5 the 5 scenarios.

Overall, the performance criteria are:

C1=Acuity in foveal vision

C2=Postural efforts

C3=Head freedom area

C4=Distortions

A weight Wj,k may be assigned to each criterion Ck, k=1, . . . , 4 that is computed in a scenario Sj, as shown in Table 1 below.

TABLE 1

|  | C1 | C2 | C3 | C4 |
| --- | --- | --- | --- | --- |
| Scenario 1 | W1, 1 | W1, 2 | | |
| Scenario 2 | W2, 1 | W2, 2 | | |
| Scenario 3 | W3, 1 | W3, 2 | | |
| Scenario 4 | | W4 ,2 | W4, 3 | |
| Scenario 5 | | | | W5, 4 |

Let us denote Vj,k the value taken by the performance criterion Ck in the scenario Sj.

At the end of the computation, the processor 14 may compute a weighted total along each row of Table 1, in order to evaluate the global performance Perf of the equipment, which, in the present non-limiting example, is along the 5 functional characteristics Q1-Q5:

$$\mathrm{Perf}(j)=\Sigma_k V_{j,k} \times Wj,k$$

where j relates to the performance characteristic in scenario Sj and k relates to the performance criterion Ck.

The above example demonstrated the use of one scenario to evaluate each characteristic of the equipment. Another embodiment can define multiple scenarios to be combined for each functional characteristic.

Figure 2:
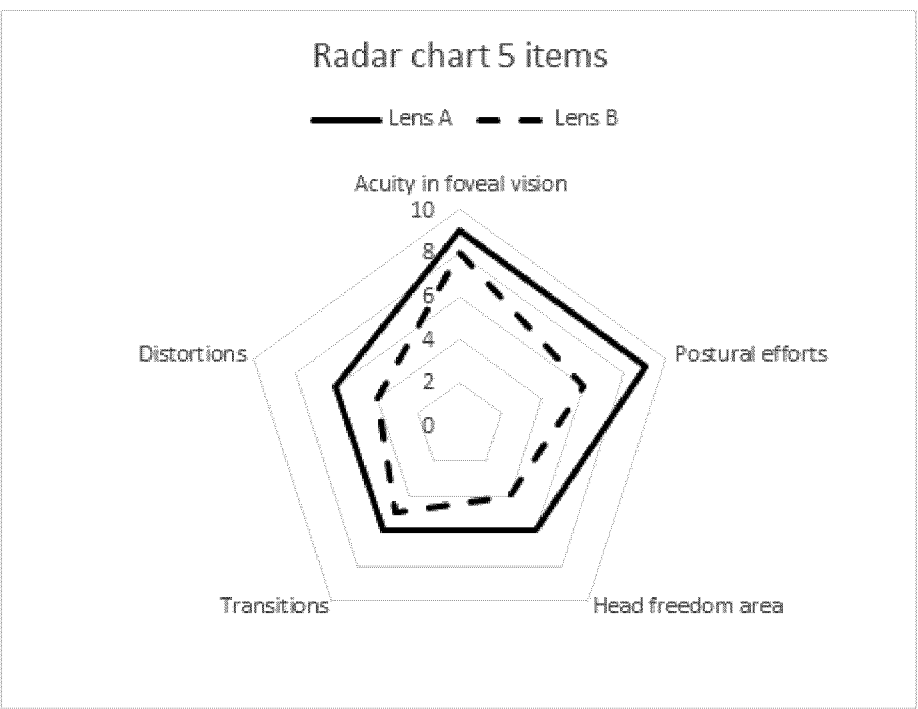
FIG. 2 is a graph illustrating another non-limiting example of multidimensional performance evaluation.

The graph of FIG. 2 illustrates a self-explanatory "radar-type" non-limiting example of multidimensional performance evaluation, for two lenses A and B.

Figure 3:
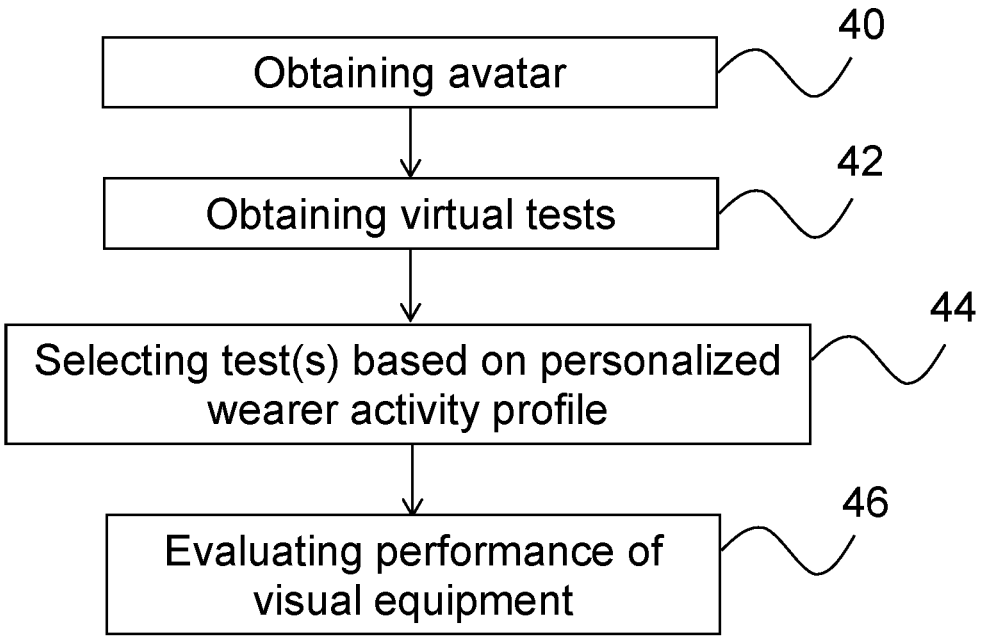
FIG. 3 is a flow diagram showing steps of a method according to the disclosure, in a particular embodiment.

The flow diagram of FIG. 3 shows steps of a method according to the disclosure for evaluating a performance of a visual equipment intended for a wearer.

A first step 40 comprises obtaining at least one avatar i.e. at least one virtual model of the wearer, as described above in relationship with the device according to the disclosure.

A following step 42 comprises obtaining a plurality of virtual tests to be performed with the visual equipment, each virtual test of the plurality of virtual tests comprising at least one scenario combined with the at least one avatar obtained at step 40, the scenario defining how a predetermined visual task comprising a sequence of fixation points is to be carried out by the at least one avatar in an environment. The at least one scenario is for example as described above in relationship with the device 10.

A following step 44 comprises selecting by at least one processor such as for example the processor 14 at least one virtual test among the plurality of virtual tests obtained at step 42, based on the at least one personalized wearer activity profile P representing usage of the visual equipment by the wearer, for example as described above in relationship with the device 10.

Then, a step 46 comprises evaluating by the at least one processor the performance of the visual equipment with which the selected at least one virtual test is performed by the at least one avatar, by computing, for at least one of the fixation points of the above-mentioned sequence, at least one predetermined performance criterion generated for the task, for example as described above in relationship with the device 10.

In a particular embodiment, the method according to the disclosure is computer-implemented. Namely, a computer program product comprises one or more sequences of instructions that are accessible to a processor and that, when executed by the processor, cause the processor to carry out steps of the method for evaluating a performance of a visual equipment intended for a wearer as described above.

The avatar and the virtual tests (comprising the scenarios) may be built for example remotely in a cloud, or locally in a computer.

The sequence(s) of instructions may be stored in one or several non-transitory computer-readable storage medium/media, including a predetermined location in a cloud.

Similarly to embodiments of the device 10 described above:

in an embodiment of the method, the avatar may comprise a virtual model of at least one eye of the wearer, a virtual model of the head of the wearer and a virtual model of the torso of the wearer;

in an embodiment of the method, the wearer is a given individual, in which case the at least one avatar comprises a virtual model of that given individual. In such a case, the avatar corresponds to a real person, sharing characteristics with that person; in that embodiment, the plurality of virtual tests may comprise multiple scenarios combined with the virtual model of the given individual;

alternatively, the wearer may pertain to a group of wearers defined by general characteristics, individual characteristics of each wearer of that group being unknown. In that case, the at least one avatar comprises a plurality of virtual models of wearers that is representative of that group of wearers. In such a case, the avatar corresponds to a group of persons; in that embodiment, the plurality of virtual tests may comprise, either a single scenario combined with the plurality of virtual models of wearers, or multiple scenarios combined with the plurality of virtual models;

in still another embodiment of the method, the wearer may not be an existing person, but a predefined average wearer, in which case the characteristics of the avatar correspond to those of that average wearer;

in an embodiment of the method, the personalized wearer activity profile P may comprise different weights assigned to the at least one scenario and/or to the at least one predetermined performance criterion depending on the relevance of the at least one scenario and/or of the at least one criterion for the wearer in the usage of the visual equipment.

Thus, by simulating a given wearer performing a variety of visual tasks through the use of the avatar, generating performance criteria for each task and combining the results, an overall estimation of the performance of a visual equipment item is obtained which takes into account the specificity of that given wearer.

Among the multiple benefits of the device, method, computer program product and computer-readable storage medium according to the present disclosure:

they may be used for assessing lens performance for a wearer;

they may be helpful e.g. to an ECP (Eye Care Professional) for selecting a lens among different available lenses, by comparing the performances thereof in order to determine which equipment is the most adapted one to the considered customer, taking into account the customer's characteristics, lifestyle and usage of visual equipment;

they may be used for helping to define a new lens design at research and development stage, using for instance different groups of wearers having different profiles, which means possibly different selections of scenarios and/or different avatars and they make it possible to obtain a performance assessment for those groups and discard design having performance scores considered too low.

Although representative methods and devices have been described in detail herein, those skilled in the art will recognize that various substitutions and modifications may be made without departing from the scope of what is described and defined by the appended claims.

The invention claimed is:

1. A device for evaluating a performance of a visual equipment intended for a wearer, wherein said device comprises: at least one input adapted to obtain a plurality of virtual tests to be performed with said visual equipment, each virtual test of said plurality of virtual tests comprising at least one scenario combined with at least one virtual model of said wearer, said scenario defining how a predetermined visual task comprising a sequence of fixation points is to be carried out by said at least one virtual model in an environment defined by a description of shapes and positions of elements to be viewed by said at least one virtual model of said wearer; at least one processor configured for: selecting at least one virtual test among said plurality of virtual tests, based on at least one personalized real or simulated wearer activity profile representing usage of said visual equipment by said wearer; evaluating said performance of said visual equipment with which said selected at least one virtual test is performed by said at least one virtual model of said wearer, by computing for at least one of said fixation points at least one predetermined performance criterion generated for said predetermined visual task.

2. The device according to claim 1, said wearer being a given individual, wherein said at least one virtual model of said wearer comprises a virtual model of said given individual.

3. The device according to claim 1, said wearer pertaining to a group of wearers defined by general characteristics, individual characteristics of each wearer of said group being unknown, wherein said at least one virtual model of said wearer comprises a plurality of virtual models of wearers that is representative of said group of wearers.

4. The device according to claim 1, wherein said personalized wearer activity profile comprises different weights assigned to said at least one scenario and/or to said at least one predetermined performance criterion depending on the relevance of said at least one scenario and/or of said at least one criterion for said wearer in said usage of said visual equipment.

5. The device according to claim 1, wherein said virtual model of said wearer comprises a virtual model of at least one eye of said wearer, a virtual model of the head of said wearer and a virtual model of the torso of said wearer.

6. The device according to claim 1, wherein said predetermined performance criterion comprises at least one of visual acuity criteria, distortion criteria and visual behavior criteria evaluating the head and eyes coordination.

7. The device according to claim 6, wherein said at least one predetermined performance criterion involves either monocular or binocular vision.

8. The device according to claim 1, wherein said at least one scenario comprises at least a first scenario for which said predetermined visual task is a far vision task and said at least one predetermined performance criterion is visual acuity, a second scenario for which said predetermined visual task is an intermediate vision task and said at least one predetermined performance criterion is visual acuity, a third scenario for which said predetermined visual task is a near vision task and said at least one predetermined performance criterion is visual acuity, and a fourth scenario for which said at least one predetermined performance criterion is a distortion criterion.

9. A method for evaluating a performance of a visual equipment intended for a wearer, wherein said method comprises: obtaining at least one virtual model of said wearer; obtaining a plurality of virtual tests to be performed with said visual equipment, each virtual test of said plurality of virtual tests comprising at least one scenario combined with said at least one virtual model of said wearer, said scenario defining how a predetermined visual task comprising a sequence of fixation points is to be carried out by said at least one virtual model in an environment defined by a description of shapes and positions of elements to be viewed by said at least one virtual model of said wearer; selecting by at least one processor at least one virtual test among said plurality of virtual tests, based on at least one personalized real or simulated wearer activity profile representing usage of said visual equipment by said wearer; evaluating by said at least one processor said performance of said visual equipment with which said selected at least one virtual test is performed by said at least one virtual model of said wearer, by computing for at least one of said fixation points at least one predetermined performance criterion generated for said predetermined visual task.

10. The method according to claim 9, said wearer being a given individual, wherein said at least one virtual model of said wearer comprises a virtual model of said given individual.

11. The method according to claim 9, said wearer pertaining to a group of wearers defined by general characteristics, individual characteristics of each wearer of said group being unknown, wherein said at least one virtual model of said wearer comprises a plurality of virtual models of wearers that is representative of said group of wearers.

12. The method according to claim 9, wherein said personalized wearer activity profile comprises different weights assigned to said at least one scenario and/or to said at least one predetermined performance criterion depending on the relevance of said at least one scenario and/or of said at least one criterion for said wearer in said usage of said visual equipment.

13. The method according to claim 9, wherein said virtual model of said wearer comprises a virtual model of at least one eye of said wearer, a virtual model of the head of said wearer and a virtual model of the torso of said wearer.

14. A computer program product for evaluating a performance of a visual equipment intended for a wearer, wherein it comprises one or more sequences of instructions that are accessible to a processor and that, when executed by said processor, cause said processor to: obtain at least one virtual model of said wearer; obtain a plurality of virtual tests to be performed with said visual equipment, each virtual test of said plurality of virtual tests comprising at least one scenario combined with said at least one virtual model of said wearer, said scenario defining how a predetermined visual task comprising a sequence of fixation points is to be carried out by said at least one virtual model in an environment defined by a description of shapes and positions of elements to be viewed by said at least one virtual model of said wearer; select at least one virtual test among said plurality of virtual tests, based on at least one personalized real or simulated wearer activity profile representing usage of said visual equipment by said wearer; evaluate said performance of said visual equipment with which said selected at least one virtual test is performed by said at least one virtual model of said wearer, by computing for at least one of said fixation points at least one predetermined performance criterion generated for said predetermined visual task.

15. A non-transitory computer-readable storage medium, wherein it stores one or more sequences of instructions that are accessible to a processor and that, when executed by said processor, cause said processor to: obtain at least one virtual model of said wearer; obtain a plurality of virtual tests to be performed with said visual equipment, each virtual test of said plurality of virtual tests comprising at least one scenario combined with said at least one virtual model of said wearer, said scenario defining how a predetermined visual task comprising a sequence of fixation points is to be carried out by said at least one virtual model in an environment defined by a description of shapes and positions of elements to be viewed by said at least one virtual model of said wearer; select at least one virtual test among said plurality of virtual tests, based on at least one personalized real or simulated wearer activity profile representing usage of said visual equipment by said wearer; evaluate said performance of said visual equipment with which said selected at least one virtual test is performed by said at least one virtual model of said wearer, by computing for at least one of said fixation points at least one predetermined performance criterion generated for said predetermined visual task.

\* \* \* \* \*